(12) United States Patent
Furze et al.

(10) Patent No.: US 7,055,363 B2
(45) Date of Patent: Jun. 6, 2006

(54) METHOD OF CALIBRATING A DETECTOR AND CALIBRATION SPHERE FOR THE SAME

(75) Inventors: Paul A. Furze, Tiverton, RI (US); Donald Laprade, Acushnet, MA (US)

(73) Assignee: Acushnet Company, Fairhaven, MA (US)

( * ) Notice: Subject to any disclaimer, the term of this patent is extended or adjusted under 35 U.S.C. 154(b) by 76 days.

(21) Appl. No.: 10/776,429

(22) Filed: Feb. 11, 2004

(65) Prior Publication Data

US 2005/0172695 A1   Aug. 11, 2005

(51) Int. Cl.
*G01D 18/00* (2006.01)
(52) U.S. Cl. ...................................................... 73/1.01
(58) Field of Classification Search .................. 73/1.01, 73/865.8, 865.6, 432.1; 356/243.1; 352/428; 702/94, 95
See application file for complete search history.

(56) References Cited

U.S. PATENT DOCUMENTS

| | | | |
|---|---|---|---|
| 4,240,620 A | 12/1980 | Tunkers | 269/24 |
| 4,445,628 A | 5/1984 | Cain | 222/66 |
| 5,223,679 A | 6/1993 | Yoo | 187/134 |
| 5,604,550 A | 2/1997 | White | 396/429 |
| 5,611,723 A | 3/1997 | Mitoma et al. | 451/6 |
| 5,703,687 A | 12/1997 | Kumagai et al. | 356/426 |
| 5,734,337 A * | 3/1998 | Kupersmit | 340/937 |
| 5,777,244 A | 7/1998 | Kumagai et al. | 73/865.8 |
| 5,903,341 A | 5/1999 | Perry et al. | 356/237 |
| 5,912,467 A * | 6/1999 | Okino | 250/491.1 |
| 6,031,933 A | 2/2000 | Kumagai | 382/141 |
| 6,450,082 B1 | 9/2002 | Sawdon | 92/23 |
| 6,462,303 B1 | 10/2002 | Brown | 219/121.69 |
| 6,462,812 B1 | 10/2002 | Heene et al. | 356/237.1 |
| 6,499,333 B1 * | 12/2002 | Ko et al. | 73/1.01 |
| 6,608,687 B1 | 8/2003 | Rulevich et al. | 356/601 |
| 6,630,998 B1 | 10/2003 | Welchman et al. | 356/394 |
| 6,768,509 B1 * | 7/2004 | Bradski et al. | 348/207.99 |
| 2003/0095178 A1 | 5/2003 | Shibayama | 348/46 |

* cited by examiner

Primary Examiner—Robert Raevis (57) ABSTRACT

A method of calibrating a detector using a calibration object having a rounded surface and indicia is disclosed. The calibration object, when coupled with a detector and analyzer, assists in minimizing image distortion caused by misalignment of the detector relative to the calibration object. A calibration object is also disclosed.

24 Claims, 4 Drawing Sheets

METHOD OF CALIBRATING A DETECTOR AND CALIBRATION SPHERE FOR THE SAME

FIELD OF THE INVENTION

This invention generally relates to a method of calibrating a detector and a calibration object. This invention more particularly relates to a method of calibrating a line scan camera detector to acquire an accurate image of a golf ball and a calibration sphere for the same.

BACKGROUND OF THE INVENTION

In recent years the inspection and analysis of goods that travel along conveyor, processing, manufacturing and assembly lines have become increasingly automated to match demands for greater production speed. Keeping up with such demands required quicker methods of performing quality control and quality assurance. Automated inspection systems perform a large portion of this work.

One type of detector used in such systems is a line scan camera. A line scan camera is a type of camera detector that can very quickly capture a single row of pixels of an object. The object is typically rotated while being scanned. The individual rows of pixels can then be assembled into a full image of the object. The assembled, flattened image looks as if the object were unwrapped. One advantage of this type of imaging system is the ease with which certain aspects of such images can be analyzed, especially by computer-aided, automated, and comparative techniques that obviate the need for manual object inspection. One application where line scan cameras are used is in the detection and sorting of produce. For example, U.S. Pat. No. 5,903,341 describes a produce grading and sorting system.

Another illustrative example is the use of line scan cameras in the manufacture of golf balls. Golf ball manufacturing typically involves a series of sequential processes performed at different processing stations. At many stages of assembly, processing, and handling, golf balls are automatically detected and imaged for comparison with paradigmatic golf ball images to ensure compliance within predetermined ranges of acceptable golf ball characteristics, including shape, color, shading, size, and appropriate printing of various indicia. Each such inspection process is monitored for quality assurance purposes. For example, U.S. Pat. No. 5,703,687 shows an automated inspection system that requires the addition of golf ball rotating equipment to the usual automated conveying equipment used to convey golf balls after an automated processing step. Another golf ball inspection system is disclosed in commonly owned U.S. Pat. No. 6,630,998 B1, which is incorporated herein by reference in its entirety. It has detectors and algorithms that allow for the automated visual testing of golf balls along each stage of the production line using a line scan camera.

Nevertheless, the spherical shape of golf balls and other round objects increases the difficulty of automated inspection of their three-dimensional surfaces because of distortion introduced into line scan images resulting from camera misalignments. When using a line scan camera, if the camera's scan line and the ball's axis of rotation are not parallel, a scanned image of the ball is distorted. Resulting images are slanted. For example, rectangular indicia that have right angles appear in the scanned images as slanted parallelograms when camera positioning is misaligned.

Likewise, if the line scan camera's scan line is not directly centered on the ball's axis of rotation, another image distortion can occur. Because the curvature of a sphere is perceptible when the scan line is focused on either side of the ball's axis of rotation, a straight vertical line drawn across the diameter of the sphere will appear curved instead of straight.

In a similar vein, if the line scan camera's scan line is not vertically centered on the ball's surface, the scanned images have yet another distortion. Because of the ball's curvature, when the scan line is not vertically centered on the ball's equatorial line as it rotates, its indicia appear to be vertically shorter in the image. Images of conforming golf ball's indicia appear shorter than comparable indicia in the paradigmatic images. Finally, a line scan camera can become unfocused, depending on the varying shapes and sizes of the scanned objects and on the varying positionings of the camera with respect to these objects.

Hence, there remains a need for an inspection system that can be calibrated to minimize distortions.

SUMMARY OF THE INVENTION

Hence, the present invention is directed to a method of calibrating a detector that minimizes image distortions.

The present invention is also directed to a method of calibrating a detector that adjusts the detector's field of view so that it is parallel to a detected object's axis of rotation.

The present invention is also directed to a method of calibrating a detector that horizontally centers the detector's field of view on a detected object's axis of rotation.

The present invention is also directed to a method of calibrating a detector that vertically centers the detector's field of view on the detected object's equatorial line.

The present invention is also directed to a method of calibrating a detector that focuses the detector according to the detected object's position, size and shape.

The present invention is also directed to a calibration object for use with the method of this invention.

The present invention is directed to a method of calibrating a detector comprising the steps of providing a calibration object having an indicium and an axis of rotation, making an image of the indicium with a detector, comparing the image with a predetermined image, and adjusting the detector so that a subsequent image of the indicium more-closely matches the predetermined image. The calibration object resembles golf balls to be inspected.

The detector, which preferably includes a line scan camera, can be adjusted to minimize a rotational misalignment of the detector, horizontal misalignment of the detector, or vertical misalignment of the detector.

The present invention is further directed to a method for calibrating a detector, comprising the steps of positioning a calibration sphere at a position on a golf ball production line occupied by a golf ball during golf ball inspection, imaging the calibration object using a line scan camera detector to produce an image, comparing the image with an predetermined image, and adjusting the detector.

The present invention is further directed to a calibration object comprising an axis of rotation, a first indicium that designates the axis of rotation, such that the first indicium, when detected by a detector, indicates whether the detector is parallel to the axis of rotation. The calibration object further includes a second indicium that designates a plane that contains the axis of rotation, such that the second indicium, when detected by a detector, indicates whether the detector is in front of the axis of rotation; and at least two indicia having a known distance apart from each other, such that, when detected by a detector, indicate a scale factor that relates a detected distance to the known distance.

The present invention is also directed to a method for calibrating an image of a calibration object rotatable by a stepper motor comprising the steps of rotating the calibration object, providing at least two indicia that form a first angle between the indicia, obtaining a digital image of the calibration object, determining a second angle between corresponding indicia on the image, determining an adjustment factor from the first and second angle and applying this adjustment factor to images of other objects, e.g., golf balls, rotated by said motor.

BRIEF DESCRIPTION OF THE DRAWINGS

In the accompanying drawings, which form a part of the specification and are to be read in conjunction therewith and in which like reference numerals are used to indicate like parts in the various views.

DETAILED DESCRIPTION OF THE PREFERRED EMBODIMENTS

As illustrated in the accompanying drawings and discussed in detail below, one aspect of the present invention is directed to a method of calibrating a line scan vision detector or camera in a golf ball inspection system. First, a calibration object that mimics a golf ball is positioned on a golf ball production line at an inspection station. Then, the inspection camera images the calibration object. Next, the calibration object image is compared with an ideal image. Finally, the spatial and focal positioning of the detector with respect to the calibration object is adjusted to minimize differences between the calibration object image and the ideal image. By adjusting the detector with respect to the calibration object, the detector is thereby calibrated to accurately inspect golf balls using images that have minimal distortion.

Figure 1:
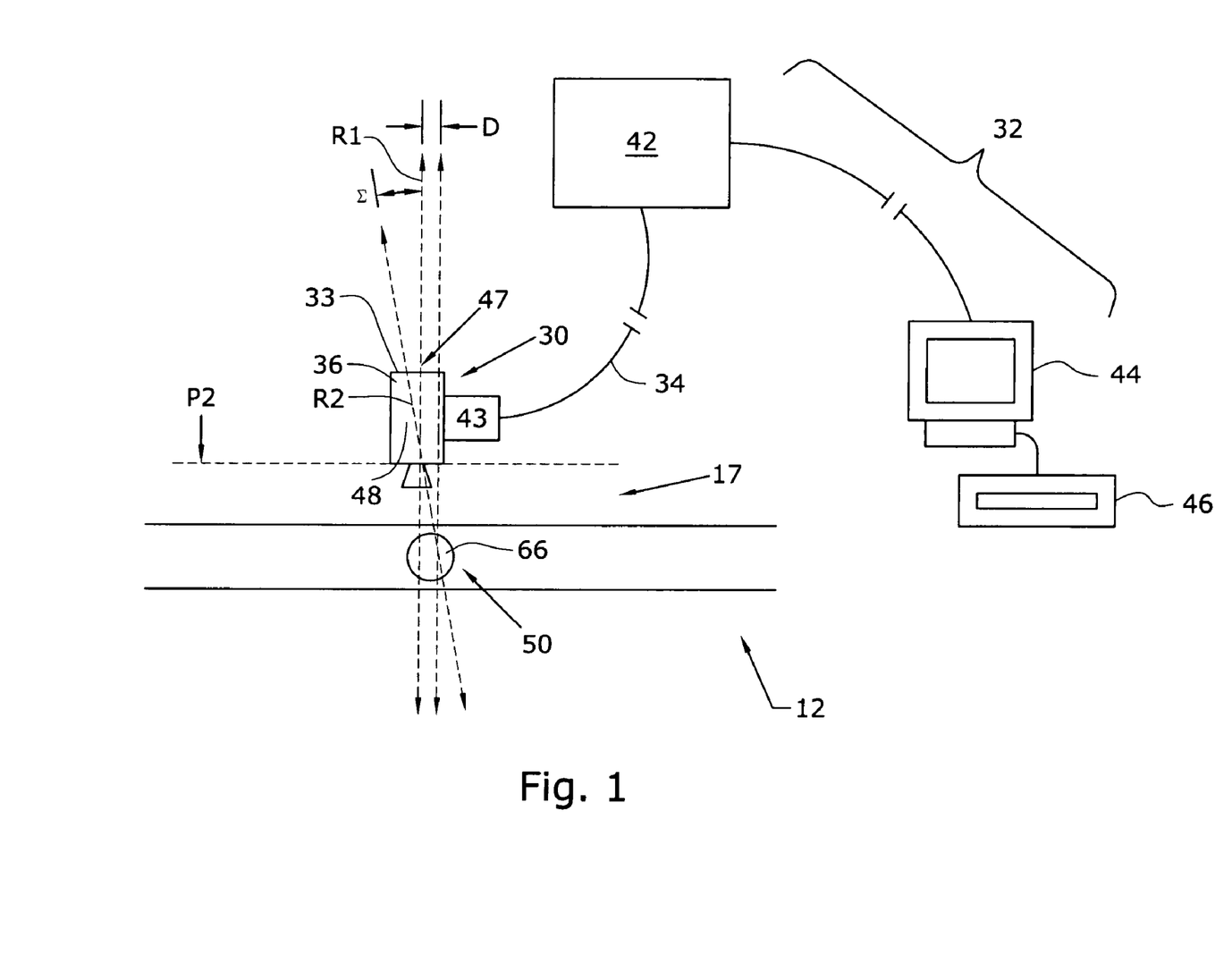
FIG. 1 is a schematic illustration of an automated golf ball inspection system in accordance with the present invention, wherein a line scan camera is rotationally, horizontally, and vertically misaligned.

An illustrative detection system to which this method can be applied is shown in FIG. 1. Golf ball production comprises several steps, and each step requires quality assurance and quality control. One suitable way to inspect golf balls is by using an automated system described in the '998 patent, previously incorporated herein by reference in its entirety. As more particularly seen in FIG. 1, automated inspection system 12 comprises an imaging system 30 and an automated analyzer 32 linked together via an electronic link 34.

In one embodiment, detector 36 of imaging system 30 views and detects golf ball 66 and provides a detection signal, i.e., data used to assemble a two-dimensional image of golf ball 66 at inspection station 17, into automated analyzer 32. Detector 36 is preferably a line scan camera suitable for analyzing golf balls. In one embodiment, camera 36 is an electronically shuttered, solid-state CCD (charged coupled device) SP-14-01k40 model line scan detector, obtainable from Dalsa, Inc. Detector 36 can pivot about axes R1 and R2 at respective pivot points 47 and 48, and can be translaterally shifted along vertical plane P2, which is perpendicular to detector 36's direction of focus. In one embodiment, camera 36 is mounted on an "X–Y" slide.

Analyzer 32 receives the detection signal from detector 36 and uses the signal to perform various analytical tasks, such as statistics processing, task scheduling, generation of reject signals or further control signals, and/or alarms. Analyzer 32 can also record the image of inspected golf ball 66 for future reference. Analyzer 32 may be placed near, and most preferably adjacent, to the operator to enable easy and quick access to both analyzer 32, to view a defect, and inspection station 17, to attend to and to correct the cause of the distortion. Analyzer 32 includes a high-speed vision engine 42, which has a computer processor, monitor 44 and keyboard 46, among other components. Vision engine 42 analyzes the image that detector 36 transmits by comparing the detected image with an ideal reference image.

Figure 2:
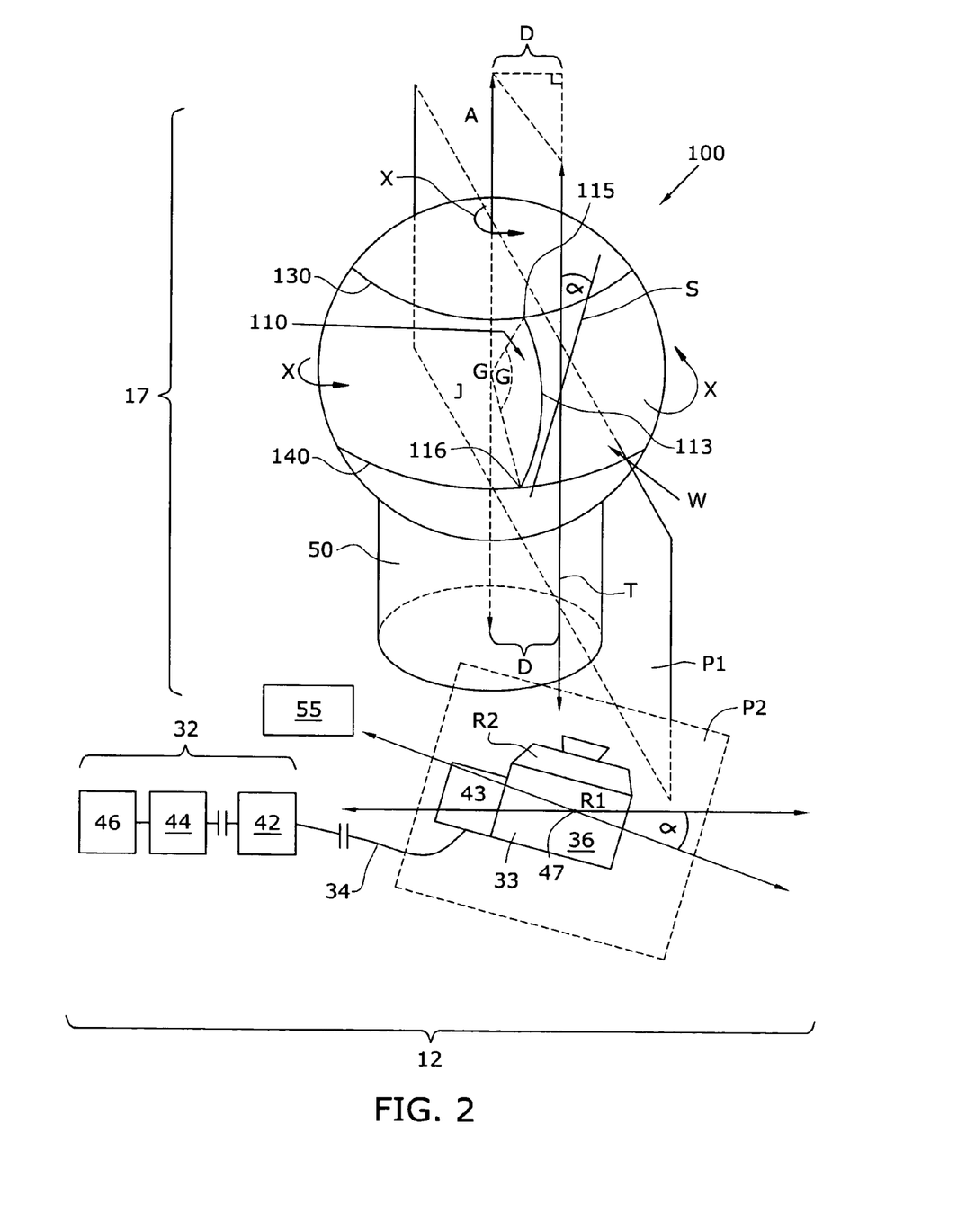
FIG. 2 includes schematic representations of the line scan camera, and the inspection system, and an enlarged calibration sphere positioned at an inspection station, in accordance with the present invention.

Referring to FIG. 2, when needed, analyzer 32 can also transmit signals to adjust camera 36 rotationally, horizontally and vertically and to focus camera 36. Camera 36 is repositioned with shift mechanism 43, which has three motors coupled to three drive wheels, each of which works to move camera 36, either rotationally at pivot point 47 about axis R1, horizontally along plane P2, or vertically up and down with respect to golf ball 66. It focuses camera 36 with a suitable automatic focusing system.

Images of inspected golf ball 66 may be displayed on monitor 44 so that the operator may compare the images to an ideal image, particularly if golf ball 66 is defective. Highlights and color error markers can be set to emphasize important features or problems in the image displayed on monitor 44. A freeze frame feature may be provided to freeze a defective ball on monitor 44 for closer scrutiny while inspection continues. Such a feature also permits the scanned image to be stored and displayed so that the operator may view the areas found defective by analyzer 32 while allowing the inspection process to continue. The frozen image remains displayed for an amount of time specified by the operator or until manually reset.

A variety of inspection routines may be performed by vision engine 42, such as finding the center of golf ball 66, checking overall dimensions and contours, inspecting for contamination, and/or determining various characteristics of a surface treatment. The specific inspection routine performed on the golf ball is selected based on the process being inspected, as is described fully in the '998 patent.

With regard to any of these routines, however, image distortions can occur through the improper positioning of detector or line scan camera 36 with respect to golf ball 66. If line scan camera 36's scan line and a ball's axis of rotation are not parallel, a scanned image of the ball would appear slanted. This distortion is caused by rotational misalignment of camera 36. If camera 36's scan line is not directly centered on the ball's axis of rotation, bowing distortion due to the curvature of ball 66 would occur. This distortion is caused by horizontal misalignment of camera 36. If camera 36 is not vertically centered on the surface of ball 66, resulting images may not match an ideal image. Inaccurate camera focus introduces blurring distortion, as well. As discussed below, one aspect of the present invention is directed to the calibration of camera 36, which is rotationally, horizontally, and vertically misaligned.

One aspect of the present invention generally includes providing a calibration object having an indicium and an axis of rotation, obtaining an image of the indicium with a detector, comparing the image with an ideal image, and adjusting the detector so that a subsequent image of the indicium more-closely matches a reference image. More specifically, it includes determining the presence, direction and degree of camera 36's misalignment, and inaccurate focusing, if any, and determining the amounts of required correction; and adjusting and focusing camera 36 according to the amounts determined. The particular embodiments described below correct the rotational, horizontal, and vertical misalignment of, and focus, camera 36.

Referring to FIG. 2, calibration sphere 100 is placed in the position occupied by golf ball 66 at inspection station 17. Calibration sphere 100 has a diameter that is substantially equal to the diameter of golf ball 66. It has longitudinal indicium 110 and latitudinal indicia 130 and 140. These indicia are used to indicate whether, and to what degree, camera 36 needs calibration. Indicium 110 is used to indicate rotational and horizontal misalignment of camera 36, and indicia 130 and 140 are used to determine vertical misalignment of camera 36. Indicia 130 and 140 are also used to indicate a distance scale factor between the required distance of horizontal camera adjustment and a pixel distance on a scanned image. All three indicia can also be used to indicate inaccurate camera focus. Ultimately, these indicia serve as guides for correcting various distortion problems due to camera misalignment with respect to sphere 100.

In another embodiment, sphere 100 has longitudinal and latitudinal indicia that are evenly spaced at 10-degree intervals about its circumference, which forms a grid. The longitudinal indicia intersect axis A. The latitudinal indicia are parallel to one another.

As more specifically described below, indicia 110, 130 and 140 are rotationally scanned by line scan camera 36 to produce a series of images while sphere 100 is rotated. Distortions in the images not only indicate the presence of misalignment, in some cases they are mathematically related to the direction and degree of the various misalignments of camera 36. When viewed, either by a human operator or as analyzed by analyzer 32 according to the formulas set forth below, these distorted images of indicia 110, 130 and 140 are used to determine the existence and amount of required adjustment.

Multiple scan line images of sphere 100 are captured, saved and referenced for viewing using automated system 12. Calibration sphere 100 is continuously scanned with line scan camera 36 to make a continuous stream of two-dimensional images. Calibration sphere 100 is centrally positioned on cup 50 to generate the stream of images, which are displayed on screen 44. Holder cup 50 rotates sphere 100 about vertical axis A in a counterclockwise direction, as indicated by arrows X. Alternately, sphere 100 can be rotated in a clockwise direction. Preferably, in another embodiment, camera 36 is synchronized with the rotation of sphere 100 using feedback from an encoder. Alternately, stepper motor 55, which drives cup 50, rotates sphere 100 such that every pulse of stepper motor 55 triggers the acquisition of a scan line by camera 36. Synchronization can be accomplished by other timing techniques. Sphere 100 also rotates at least one revolution per image while line scan camera 36 scans sphere 100 under scan line S.

As sphere 100 rotates, camera 36 specifically scans indicia 110, 130 and 140, each of which is represented in the images subject to various types and degrees of distortion. In response to the distortions evident in the images, an operator adjusts camera 36 while watching the images. When indicium 110 appears slanted in the images, then camera 36 is rotationally misaligned. When indicium 110 also appears bowed, then camera 36 is horizontally misaligned. When indicia 130 and 140 are not vertically centered in the images, then camera 36 is vertically misaligned. Camera 36 is adjusted to take the curve and angle distortion out of the projected images of indicium 110 and to vertically center the images on screen 44 by using latitude lines 130 and 140 on display screen 44 as guides. Vertical centering helps make sure that camera 36 is appropriately centered on ball 66 so that image taken during actual golf ball inspection match paradigmatic golf ball images. To improve the results, analyzer 32 can project a straight line or another overlay on monitor 44, next to the images of indicium 110, as a reference. By watching monitor 44, the operator can also focus the images.

Referring to FIGS. 3, 4, 5, 6, and 7, five such images are respective images 200, 300, 400, 500, and 600, each of which shows various degrees of distortion because of camera 36 misalignment and inaccurate focus, at various stages of its adjustment. Each image comprises a pixel grid of assembled scan lines, beginning with first scan lines 220, 320, 420, 520, and 620, and ending with last scan lines 225, 325, 425, 525, and 625, respectively. These scan lines more or less appear as horizontal in these figures. Each image also has respective line representations 210, 310, 410, 510, and 610 of indicium 110, and respective line representations 230 and 240, 330 and 340, 430 and 440, 530 and 540, and 630 and 640 of respective latitudinal indicia 130 and 140.

Figures 3, 4:
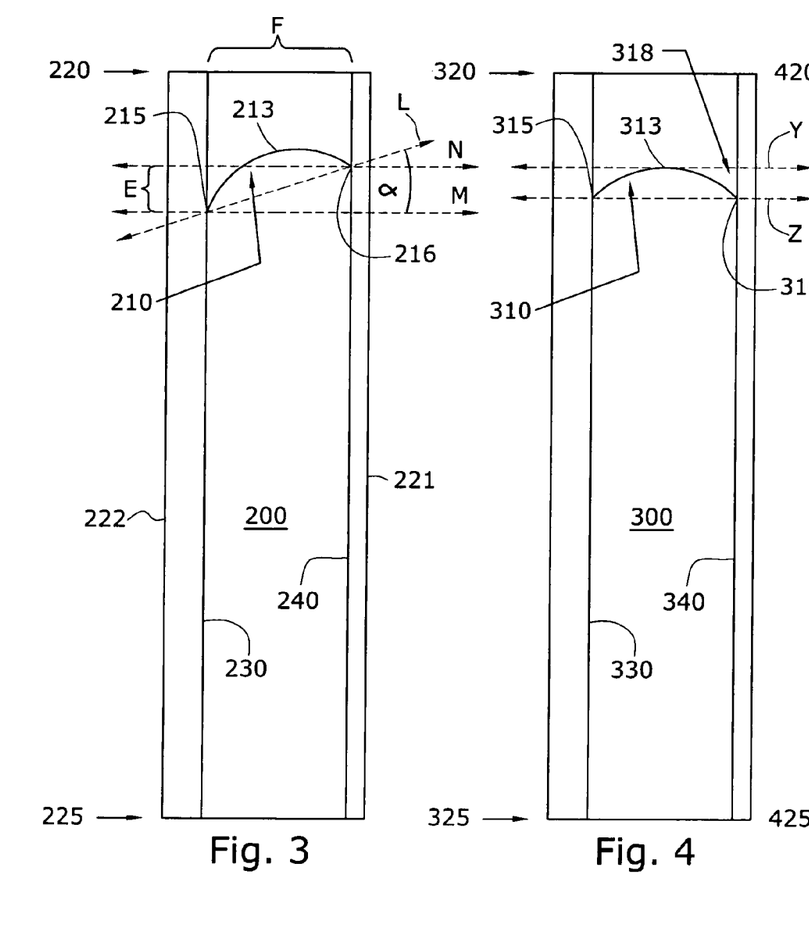
FIG. 3 is a plan view of a line scan image made by the line scan camera showing (1) slant distortion of a longitudinal indicium because the camera is rotationally misaligned; (2) bowing distortion of the longitudinal indicium because the camera is horizontally misaligned to the right of the sphere's axis of rotation; and (3) vertical misalignment because the scan line is not vertically centered.
FIG. 4 is a plan view of a line scan image after the camera is rotationally adjusted, in accordance with the present invention.
Figure 5:
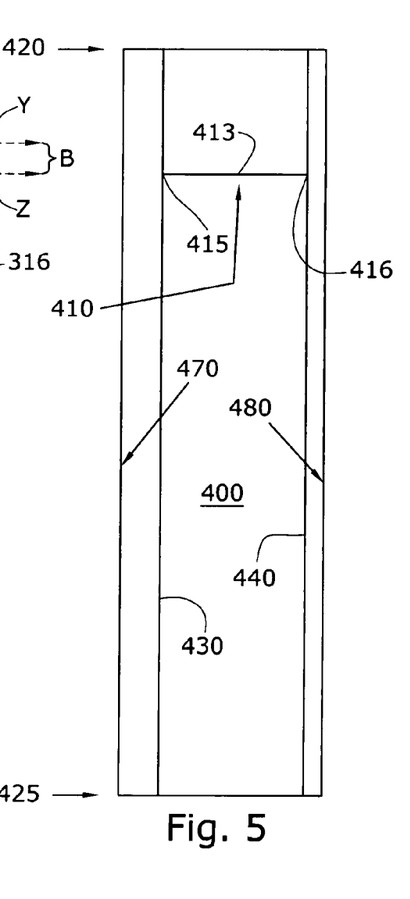
FIG. 5 is a plan view of a line scan image after the camera is rotationally and horizontally adjusted, in accordance with the present invention.
Figure 6:
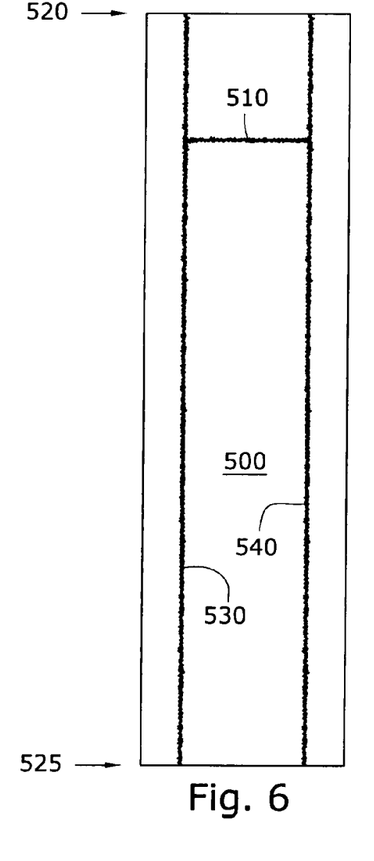
FIG. 6 is a plan view of a line scan image after the camera is rotationally, horizontally, and vertically adjusted, and after the camera has become unfocused, in accordance with the present invention.

Referring to FIG. 3, image 200 indicates that camera 36 is rotationally, horizontally, and vertically misaligned. The fact that line 210 is slanted away from line M along line L indicates that camera 36 is rotationally misaligned. By bowing, line 210 also indicates that camera 36 is horizontally misaligned. And by being positioned closer to image edge 221 than edge 222, lines 230 and 240 indicate that camera 36 is vertically misaligned. Referring to FIG. 4, image 300, which is taken after camera 36 is rotationally adjusted, indicates that camera 36 is still horizontally and vertically misaligned, as shown by the bowing of line 310 and uncentered lines 330 and 340. Referring to FIG. 5, image 400, which is taken after rotational and horizontal adjustment of camera 36, shows only vertical misalignment by its uncentered lines 430 and 440. Referring to FIG. 6, after camera 36 vertically adjusted, however, image 500 indicates that camera 36 is rotationally, horizontally, and vertically adjusted. However, camera 36 might have become unfocused during vertical adjustment, as shown by blurred lines 510, 530 and 540 in image 500. Camera 36 is accordingly focused, as shown in image 600 of FIG. 7. These adjustments, and how images 200, 300, 400, 500, and 600 indicate camera 36 misalignment and inaccurate focusing, are described below.

As shown in FIGS. 1 and 2, camera 36 is rotationally, horizontally, and vertically misaligned. It is rotationally misaligned with respect to sphere 100 about its axis of rotation R1, by α degrees. Thus, scan line S is not parallel to axis of rotation A. This introduces slant distortion in every image produced by camera 36 until it is rotated by a about axis R1. Camera 36 is also horizontally misaligned with respect to rotational axis A by distance D. This misalignment causes bowing distortion in every image taken by camera 36 until it can be horizontally shifted (or rotated) to its correct position wherein scan line S is focused directly on axis A. Camera 36 is also vertically misaligned such that its images will not correctly match paradigmatic images. Before its horizontal and vertical misalignments are adjusted, preferably the rotational misalignment of camera 36 is adjusted to minimize slant distortion. Referring to FIG. 3, line 210 in image 200 depicts the rotational distortion of camera 36 by depicting vertical indicium 110 as slanted. Referring to FIG. 2, this slanting occurs because, as indicium 110 rotates towards scan line S, first line end 116, and then second line end 115, pass under scan line S. Referring to FIG. 3, corresponding line end 216 is accordingly closer to first pixel row 220 than line end 215. Instead of depicting indicium 110 as a straight, vertical line, indicium 110 is depicted as bowed and slanted line 210.

To correct this slant distortion, in one embodiment the operator manually adjusts camera 36 by viewing monitor 44 and rotating the camera 36 about R1 until slant distortion no longer appears in the images. Referring to FIG. 2, by so doing the operator rotates camera 36 so that scan line S lies along line T. Thus, indicium 110 acts as a guide, much like a plumb line, as to the degree of required rotation. When imaged multiple times, it provides a base of comparison for accurate camera repositioning during this process.

Referring to FIGS. 1 and 2, in an alternate embodiment, camera 36 is automatically adjusted by rotating camera 36 about R1, using shifting mechanism 43 to receive commands from analyzer 32 and to rotate camera 36. Referring to FIG. 3, using horizontal pixel distance E between line ends 215 and 216 (shown between lines N and M), and vertical pixel distance F between image lines 230 and 240, angle α is automatically calculated. The direction of automatic rotation is determined by factoring in the rotational direction of sphere 100 and the relative scan order of ends 116 and 115. Because line end 116 was scanned before line end 115, and nearest surface W of sphere 100 moved to the right with respect to camera 36, analyzer 32 determines that camera 36 is to be rotated counterclockwise as viewed from its rear panel 33. According to these calculations and variables, suitable analysis and automation routines can be calculated and performed to rotationally adjust camera 36. Any pivot mountings and control equipment suitable to receive commands from analyzer 32 and to rotate camera 36 may be used.

In another embodiment, analyzer 32 commands suitable control equipment to rotate camera 36 until images of line ends 215 and 216 define a line perpendicular to corresponding images of latitudinal lines 230 and 240. Alternately, any suitable image line relationship in one of the captured images that indicates rotational alignment can be used to control the amount of automated rotation.

Referring to FIG. 4, even though camera 36 is rotationally adjusted, line 310 still bows. Referring to FIG. 2, indicium 110 appears to bow because of distortion due to the three-dimensional curvature of sphere 100 whenever camera 36 does not focus scan line S on rotational axis A. Longitudinal indicium 110 defines plane P1 in which rotational axis A lies. Thus, indicium 110 can appear straight to the naked eye, but only when viewed from a perspective in plane P1. For example, when viewed roughly from behind and above camera 36 as shown, indicium 110 must lie directly between axis A and the viewer, or indicium 110 will appear curved because of the rounded face of sphere 100 if sphere 100 is not transparent. From the perspective in FIG. 2, sphere 100 must be rotated clockwise along axis A for indicium 110 to appear straight.

Similarly, because scan line S passes over only one row of pixels at a time, all of indicium 110 must pass in front of scan line S at the same time for it to appear straight in a scanned image. This also is because of the curvature of sphere 100. Because of the curvature of sphere 100, if camera 36 does not point scan line S directly towards axis of rotation A, indicium cannot entirely pass under scan line S at one time. Therefore, for image lines of indicium 110 to appear straight (i.e. undistorted), scan line S must be centered in the direction of rotational axis A.

As with rotational adjustment, indicium 110, because it lies in the same plane P1 as axis A, serves as a guide for horizontal adjustment. In one embodiment, the operator manually repositions camera 36 to the left or right along plane P2, while viewing a stream of images depicting indicium 110, until the images of indicium 110 no longer bow.

Referring to FIG. 4, in an alternate embodiment, the horizontal adjustment of camera 36 is automated. In terms of direction and distance, line image 310 denotes sufficient information to calculate the proper distance D that camera 36 should be moved for automatic adjustment as controlled by analyzer 32. The horizontal distance to move camera 36 is given in the formula below:

$$D=(C)(B)/(1-\cos \ominus/2)$$

where (1) D is the horizontal distance to move camera 36; (2) ⊖ represents the angle from center G of sphere 100 to end points 115 and 116 of indicium 110 in terms of degrees of latitude between latitudinal indicia 130 and 140 as measured from sphere center G (see FIG. 2); (3) B is the bow distance measured between the most-bowed point of line 310 (line center 313) and either of its two least-bowed points (line ends 115 and 116) along either of lines 330 or 340; and (4) C is an image distance-to-actual distance scale factor coefficient.

Distance B on image 300 must be scaled to account for differences between distance B on image 300 and the actual distances between indicia 130 and 140 on sphere 100 according to calculated scale factor C. Images 330 and 340 of latitudinal indicia 130 and 140 are used to determine the relationship between each pixel in image 300 and the actual distance between indicia 130 and 140. Dividing the number of pixels 318 between lines 330 and 340 by the known distance between indicia 130 and 140, usually in mm, yields scale factor C in pixels per mm. Scale factor C is used to accommodate differences in apparent sphere size from one imaging system to another imaging system, or when mechanical changes are made to a system that might affect an image, like changing a camera or lens. Thus, in accordance with the equation set forth above, distance D is directly related to the bow distance B, which is equal to the length of image 300, as measured along either of imaged lines 330 or 340, that lies between lines Y and Z.

In one embodiment, once the amount of horizontal misalignment is automatically determined, the operator manually adjusts the horizontal position of camera 36. Adjusting to correct the horizontal misalignment of camera 36 requires that the operator shift camera 36 to the right by an exact distance equal to distance D.

In other words, camera 36 is shifted in the same direction as the rotational movement of nearest surface W of sphere 100 to camera 36, by a distance D. Such a shift is translateral, i.e., parallel with respect to plane P2, which is defined by the field of view of camera 36. The calibration process of imaging sphere 100, which includes determining the direction and degree of adjustment and manually adjusting, is repeated until further image lines no longer bow. Alternately, the shift can be rotational if the axis of rotation of sphere 100 is parallel to the axis of the camera.

In an alternate embodiment, analyzer 32, through an automated command and suitable automatic shifting mechanism, shifts camera 36 to the right by distance D so that it is horizontally adjusted.

As differentiated from the separate latitudinal indicia described above, in another embodiment, two indicia used to determine scale factor C and to focus camera 36 are part of a single distinct marking, such as line ends 115 and 116 on indicium 110. It is understood that indicia that perform these functions can alternatively be any two indicia placed anywhere or in any fashion on sphere 100.

Referring to FIG. 1, in another embodiment, camera 36 is adjusted to minimize distortion due to horizontal misalignment by rotating it Σ degrees about axis of rotation R2.

Referring to FIGS. 2, 5, and 6, regarding the vertical misalignment of camera 36, scan line S is vertically off center with respect to indicia 130 and 140. Vertical misalignment of camera 36 hinders it from detecting images that can be meaningfully compared with paradigmatic golf ball images. Unless scan line S is positioned such that the center of a golf ball surface is proximate to the vertical center of a detected image, meaningful comparison of images is difficult. When imaged, indicia 130 and 140 indicate this problem. In FIG. 5, lines 430 and 440, which are shifted away from edge 470 and towards edge 480 in image 400, indicate the vertical misalignment of camera 36. To correct it, the operator adjusts camera 36 by lowering camera 36 while watching displayed images until scan line S is vertically centered about indicia 130 and 140. Referring to FIG. 6, the resulting image 500 shows that camera 36 is vertically aligned by its straight, albeit blurred, lines 510, 530 and 540.

On the other hand, scan line S can be positioned such that the center of a golf ball surface is where the vision inspection system expects it. For example, the center of the golf ball can be off-centered if this is where the vision inspection system expects to find it. Vision engine 42 can compensate for this effect by software.

Referring to FIGS. 1 and 2, in an alternate embodiment, camera 36 is automatically, vertically adjusted by analyzer 32 using shifting mechanism 43. Any device suitable for lowering and raising scan line S with respect to sphere surface W may be used, however.

In another alternate embodiment, vertical distortion is digitally adjusted by analyzer 32. Analyzer 32 locates midpoint J between lines 130 and 140 and accordingly converts the line scan data to account for vertical distortion. A point at X distance from an image representation of midpoint J is converted to X' according to the following formula:

$$X_{adj} = R \; \text{ArcSine}(X_i/R)$$

where $X_i$ is the observed distance along coordinate axis X of distorted image 400, R is the radius of ball 66 in mm, and $X_{adj}$ is the new, adjusted distance along coordinate axis X of adjusted image 500. All pixel data in image 400 is adjusted or corrected according to this formula to produce new pixel data that is displayed in image 500. This adjustment is fully described in commonly-owned, co-pending patent application entitled "Method of Inspecting a Sphere Without Orienting the Sphere," filed on even date herewith. This application is incorporated herein by reference in its entirety.

Figure 7:
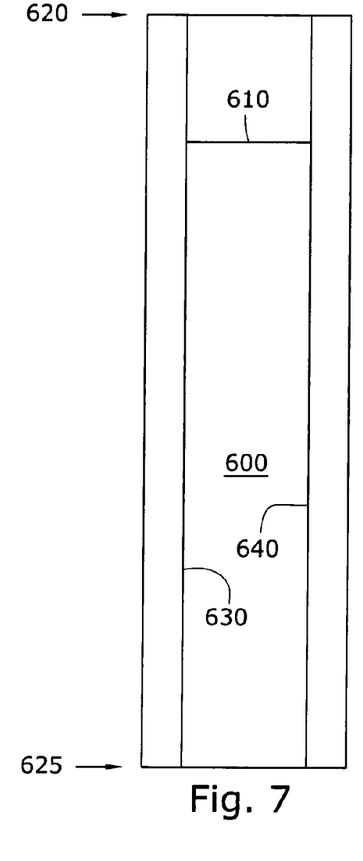
FIG. 7 is a plan view of a line scan image after the camera is focused.

Referring to FIGS. 2, 6, and 7, regarding the focusing of camera 36, latitudinal indicia 130 and 140 are respectively represented as lines 430 and 440 in image 400. As with the horizontal and rotational calibrating methods described above, focusing of camera 36 involves a comparison of a scanned image with an ideal image. Once rotational, horizontal, and vertical adjustment is complete, images can become blurred, such as in FIG. 6. The operator compares blurred lines 530 and 540 in image 500 with lines in subsequent images after the operator manually adjusts the focus on camera 36. This process is repeated until camera 36 is accurately focused, resulting in a focused image, such as image 600 in FIG. 7.

In an alternate embodiment, camera 36 is automatically focused with software and a device suitable for focusing line scan camera 36.

Figure 8:
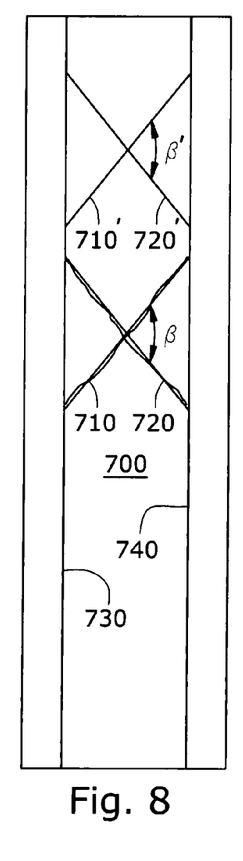
FIG. 8 is a plan view of a line scan image calibrated for stepper motor distortion.

Another type of distortion can be caused by stepper motor 55's non-linearity. Typically, stepper motor 55 follows the instructions given to it. For example, if vision engine 42 instructs the motor to rotate one revolution in a predetermined time, it would do so. However, the rotor of a stepper motor is coupled to the stator via a magnetic field. The coupling force between the rotor and the stator resembles a magnetic clutch, i.e., there can be a discernable lag between the motions of the rotor and the stator. In effect, when the rotor moves ahead of its instructed position, the image can appear compressed in that area. When the rotor lags behind where it should be, the image will appear stretched out or expanded. As shown in FIG. 8, indicia 710 and 720 are the expanded and compressed distortions of indicia 710' and 720', respectively, as they would appear on a calibration object. Indicia 710' and 720' are also superimposed on to indicia 710 and 720 to illustrate the distortions.

The stepper motor non-linearity distortion can be corrected by coupling the stepper motor to an encoder. The encoder has the ability to read back the true position of the rotor to compensate the distortion. In accordance with another aspect of the present invention, this distortion can be adjusted with calibration.

The inventors of the present invention have observed that this distortion is consistent from image to image, as long as the load is the same and the motion has the same acceleration, deceleration and speed. The solution is to take a calibration image that depicts the distortion introduced by non-linearity, calculate the adjustments needed to correct the image, and apply those corrections to every image thereafter. The calibration image should contain at least two diagonal indicia, such as indicia 710 and 720, which make an angle β to each other, as illustrated in FIG. 8. To compensate for the non-linearity distortion, angle β should be as close as practicable to angle β' between indicia 710' and 720'. A correction factor can be derived from a comparison between β and β' and this correction factor can be stored in vision engine 42 to be applied to subsequent images. Other correction techniques or adjustments can be made, such as the adjustment techniques described in co-pending patent application entitled "Method of Inspecting a Sphere Without Orientating the Sphere," previously incorporated herein by reference. This calibration technique is applicable to line scan camera, as well as area scan camera.

Additionally, in accordance with this aspect of the present invention, the calibration object preferably is cylindrical, instead of spherical to obviate any additional complexity due to spherical distortions. The cylindrical calibration object should have the same rotational inertia as a golf ball so that the stepper motor behaves the same during calibration as in operation.

In addition to its use to calibrate line scan cameras used for golf ball inspection, this method can be used to calibrate any detector that inspects objects having a rounded surface. Suitable detectors include any detectors that can inspect any such objects that travel along assembly, conveyor, production, or distribution lines.

A second aspect of the present invention is directed to a calibration object that calibrates a line scan vision detector. In one embodiment, the calibration object mimics a golf ball and is suitable for positioning at the same position occupied by a golf ball during golf ball inspection. This calibration object has at least one surface with roughly similar spatial dimensions as a golf ball. It further has indicia that indicate horizontal, rotational, and vertical misalignment of a detector with respect to the golf ball during golf ball inspection. It also has indicia that indicate and assist in correcting an inaccurate detector focal position.

A preferred embodiment is calibration sphere 100 as shown in FIG. 2 and described above. Longitudinal indicium 110 can be used to help center camera 36 so that its scan line S is directly in front of ball 66, and so that scan line S is parallel to ball 66's axis of rotation. In addition, latitudinal indicia 130 and 140 can be used to help focus camera 36. Ultimately, indicia 110, 130 and 140 can be used to determine the proper horizontal and rotational positioning, as well as focal disposition, of line scan camera 36 on golf ball inspection system 12.

It is noted, however, that the embodiments illustrated in the accompanying figures and described above do not limit the type of objects for which the method or calibration object of this invention may be used. In fact, a calibration object's surface can be any non-planar surface of rotation such as any portion of a sphere, a football, an hourglass, a cone, or a pair of cones. In a similar vein, the calibration object's surface can be either wholly or partially spherically shaped, football-shaped, hourglass-shaped, or conically shaped. It can comprise any combination of these shapes, such as having cylindrical spherical and conical portions, or dual conical portions, or any other combination thereof. In one embodiment, for instance, a ring may be used and the sides of the ring may constitute a pair of lines of longitude.

Calibration objects in accordance with the present invention can thus be used to mimic any object having an axis of rotation, even if such objects are irregularly sized. Such objects include, but are not limited to, natural products such as fruits, vegetables, smoothed rocks, or gems, either cut or uncut. They also include innumerable articles of manufacture such as toys, sporting goods, novelties and other articles of assembly. They include articles such as hardware and components including bolts, nuts, cogs, gears, screws, wheels, knobs, handles, drill bits, augers, ball bearings, chucks, and casings. They further include plastics, rubber goods, tires, hubs, break shoes, containers, bottles, caps, bowls, jars, vases and any other objects having non-cylindrical, rounded surfaces or surface portions. Thus, objects contemplated for use with the present invention also include, but are by no means limited to, rings, hoops, watch faces or any other items—whether produced, packaged, conveyed, shipped, discovered, grown or found—that have a rounded, non-cylindrical aspect to one of their surfaces or surface portions.

Indicia on a calibration object of the present invention can be any marking, whether discernable through visible light, infrared, ultraviolet, other electromagnetic radiation, electric, magnetic, sonic impulse, pressure impulse or any other detection medium or device. Indicia can therefore comprise letters, numbers, lines, curves, dots or any other type of marking.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments that would come within the spirit and scope of the present invention.

We claim:

1. A method of calibrating a detector, comprising:
providing a calibration object that mimics a golf ball having an indicium and an axis of rotation;
making an image of the indicium with a detector;
comparing the image with a predetermined image; and
adjusting the detector so that a subsequent image of the indicium more-closely matches the predetermined image.

2. The method of claim 1 wherein the detector is adjusted to minimize a rotational misalignment of the detector.

3. The method of claim 2 wherein the detector is a line scan camera and the indicium indicates whether a scan line of the camera is parallel to the axis of rotation.

4. The method of claim 1 wherein the detector is adjusted to minimize a horizontal misalignment of the detector.

5. The method of claim 4 wherein the detector is a line scan camera and the indicium indicates whether a scan line of the camera is in front of the axis of rotation.

6. The method of claim 1 wherein the detector is adjusted to minimize a vertical misalignment of the detector.

7. The method of claim 6 wherein the detector is a line scan camera and the indicium indicates whether a scan line of the camera is vertically aligned.

8. The method of claim 6 wherein the calibration object comprises latitudinal indicia that indicate whether the scan line is vertically aligned.

9. The method of claim 1 wherein the indicium indicates whether the detector is out of focus.

10. The method of claim 1 wherein the indicium comprises a longitudinal line.

11. The method of claim 1 wherein the calibration object has a surface, a portion of which is spherically shaped.

12. The method of claim 1 wherein the step of comparing the first indicium image with the predetermined image is performed using a display device.

13. The method of claim 1 wherein the detector is automatically adjusted using a shift mechanism.

14. The method of claim 13 wherein the calibration object has at least two indicia that have a known distance apart from each other, which indicate a scale factor that relates a detected distance to the known distance when detected by the detector.

15. The method of claim 14 wherein the at least two indicia are part of one indistinct marking.

16. A method for calibrating a detector, comprising:
positioning a calibration sphere at a position on a golf ball production line occupied by a golf ball during golf ball inspection;
imaging the calibration object using a line scan camera detector to produce an image;
comparing the image with an predetermined image; and
adjusting the detector.

17. The method of claim 16 wherein the detector is adjusted to minimize horizontal misalignment of the detector.

18. The method of claim 16 wherein the detector is adjusted to minimize rotational misalignment of the detector.

19. The method of claim 16 wherein the detector is adjusted to minimize vertical misalignment of the detector.

20. The method of claim 16 wherein the detector is adjusted to focus the detector.

21. A method for calibrating an image of a calibration object rotatable by a device comprising the steps of:

rotating the calibration object with the device;
providing at least two indicia that make a first angle with each other;
obtaining a digital image of the calibration object;
determining a second angle between the corresponding indicia on the image;
determining an adjustment factor from the first and second angle;
applying said adjustment factor to images of other objects rotated by said device.

22. The method of claim 21 wherein the device is a stepper motor.

23. The method of claim 21 wherein the calibration object is a cylindrical shaped object.

24. The method of claim 21 wherein the at least two indicia comprises linear-lines.

* * * * *